United States Patent [19]

Lafon

[11] Patent Number: 5,250,543

[45] Date of Patent: Oct. 5, 1993

[54] DERIVATIVES OF 1,4-DIHYDROPYRIDINE, THEIR PREPARATION PROCEDURE AND THERAPEUTIC COMPOSITIONS CONTAINING THEM

[75] Inventor: Louis Lafon, Paris, France

[73] Assignee: Laboratoire L. Lafon, Maisons Alfort, France

[21] Appl. No.: 818,037

[22] Filed: Jan. 8, 1992

[30] Foreign Application Priority Data

Jan. 9, 1991 [FR] France .................... 91 00201

[51] Int. Cl.$^5$ ................ A61K 31/445; C07D 401/02; C07D 401/14
[52] U.S. Cl. .................... 514/318; 514/343; 546/194; 546/281
[58] Field of Search ............. 546/194–281, 546/205, 206; 514/321, 318, 343

[56] References Cited

U.S. PATENT DOCUMENTS 3,985,758  10/1976  Murakami ............. 546/321
4,808,603  2/1989   Eichenberger ........ 546/152

FOREIGN PATENT DOCUMENTS 0106275  4/1984   European Pat. Off. .
0214094  8/1986   European Pat. Off. .
0266922  10/1987  European Pat. Off. .
3303066  12/1984  Fed. Rep. of Germany .
2-138257 5/1990   Japan .
2014134  1/1979   United Kingdom .

OTHER PUBLICATIONS

Hideo Sugano, (Teijin K.K.), 1,4-Dihydropyridine-3,-5-Dicarboxylic Acid Diester Derivative, Its Preparation & Pharmaceutical . . ., Patent Abstracts of Japan, vol. 9, No. 233, Sep. 19, 1985.

Primary Examiner—Bernard Dentz
Assistant Examiner—Celia Chang
Attorney, Agent, or Firm—Wegner, Cantor, Mueller & Player

[57] ABSTRACT

The invention relates to compounds having the formula:

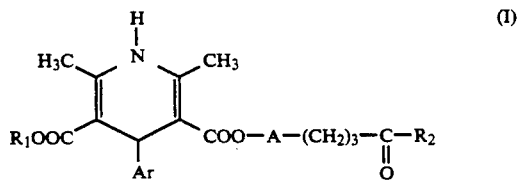

in which
Ar represents a group selected from 2-nitrophenyl, 3-nitrophenyl, 2-chlorophenyl, 2,6-dichlorophenyl, 2-trifluoromethylphenyl and 3-trifluoromethylphenyl;
$R_1$ represents a $C_1$–$C_4$ alkyl group or a group having the formula:

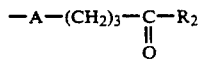

A represents a group selected from groups having the formulae:

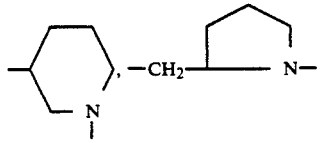

and
$R_2$ represents a group selected from 2,4,6-trimethoxyphenyl, 2-thienyl and phenyl, and their addition salts with pharmaceutically acceptable acids.

These compounds are calcium inhibitors with therapeutic applications.

7 Claims, No Drawings

DERIVATIVES OF 1,4-DIHYDROPYRIDINE, THEIR PREPARATION PROCEDURE AND THERAPEUTIC COMPOSITIONS CONTAINING THEM

The present invention relates to new derivatives of 1,4-dihydropyridine.

Various derivatives of 1,4-dihydropyridine have already been described. In particular, in FR 2 218 107 various esters of 2,6-dimethyl-4-(3-nitrophenyl)-5-methoxycarbonyl-1,4-dihydropyridine-3-carboxylic acid and notably 2-[methyl(phenylmethyl)aminolethyl ester, known as nicardipine, have already been described.

Nicardipine is known to be a calcium inhibitor and is used therapeutically as a vasodilator and an antihypertensive agent.

The aim of the present invention is to provide new calcium inhibitors which have a significant and prolonged antihypertensive action.

The present invention therefore provides compounds having the formula:

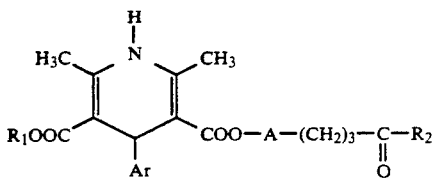

in which:

Ar represents a group selected from 2-nitrophenyl, 3-nitrophenyl, 2-chlorophenyl, 2,6-dichlorophenyl, 2-trifluoromethylphenyl and 3-trifluoromethylphenyl;

$R_1$ represents a $C_1-C_4$ alkyl group or a group having the formula:

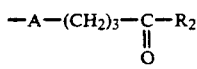

A represents a group selected from groups having the formulae:

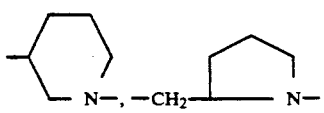

and $R_2$ represents a group selected from 2, 4, 6-trimethoxyphenyl, 2-thienyl and phenyl, and their addition salts with pharmaceutically acceptable acids.

The invention covers not only the racemic mixtures of formula I but also all stereoisomers associated with the presence of the asymetric carbon atom and possibly with rotational hindrance of certain bonds.

The expression "addition salts with pharmaceutically acceptable acids" refers to salts which, in their free base form, have biological properties without having any undesirable effects. Notably, these salts may be those formed with mineral acids such as hydrochloric acid, hydrobromic acid, sulphuric acid, nitric acid and phosphoric acid, acid metal salts such as disodium orthophosphate and monopotassium sulfate, and organic acids.

The compounds of formula I may be obtained by reacting on an acid having the formula:

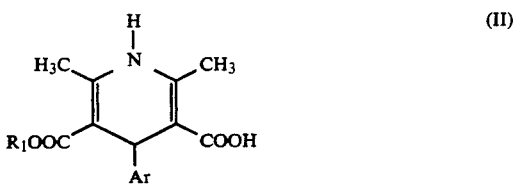

in which Ar and $R_1$ have the meaning given previously; an alcohol having the formula:

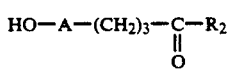

in which $R_2$ has the same meaning as before.

The addition salts are obtained by the classic reaction of a compound of formula I with a pharmaceutically acceptable acid in a suitable solvent. Inversely, the bases may be obtained from the addition salts by treatment with a strong base.

The acids of formula II may be obtained by the classic reaction of an aldehyde having the formula:

Ar—CHO    (IV)

with 2-cyanoethyl acetoacetate and a 3-aminocrotonate having the formula:

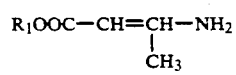

in order to obtain a compound with the formula:

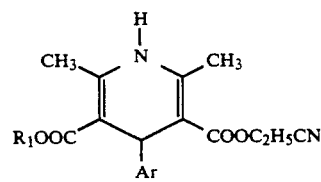

and the monohydrolysis of this diester.

The alcohols of formula III may be obtained by condensing a 3-chloropropane having the formula:

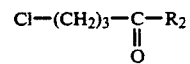

with a hydroxyamine:

HO—A—H    (VIII)

The compounds of formulae II and III may also be obtained by stereospecific syntheses. A compound of formula II may therefore be prepared stereospecifically by the following method:

by reacting an aldehyde of formula IV with an alkyl acetoacetate and ammonia according to the method of Hantzsch in order to obtain a compound having the formula:

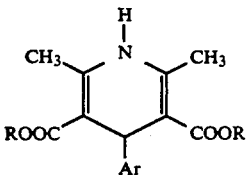

by treating the compound of formula IX with chloromethyl ethyl ether in the presence of sodium hydride in tetrahydrofuran in order to obtain a compound having the formula:

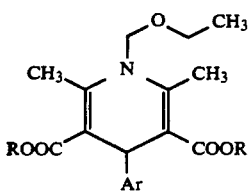

by partially hydrolysing, for example in a 1-dimethylamino-2-propanol/sodium/water mixture in order to obtain a racemic mixture having the formula:

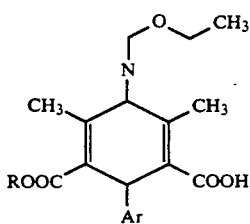

by resolving the racemic mixture by recrystallizing its salt with an optically active base;

by transforming the isomer in the form of an acid salt.

The following examples illustrate the preparation of the compounds of the invention.

EXAMPLE 1

Preparation of 2,6-dimethyl-4-(3-nitrophenyl)-5-methoxycarbonyl-1,4-dihydropyridine-3-carboxylic acid N-[3-(2,4,6, trimethoxybenzoyl)propyl]piperidine-3'-yl ester, hydrochloride (CRL 41695)

a) Preparation of 2-cyanoethyl acetoacetate

A mixture of 16.33 g (0.23 mole) of 3-hydroxy-propionitrile and 28.4 g (0.20 mole) of 2,2,6-trimethyl-1,3-dioxen-4-one in the presence of 0.1 ml of triethylamine is heated to 90°-100° C. for 4 hrs 30 mins.

The reaction product is purified by distillation under reduced pressure, producing 23.3 g of a pale yellow oil.

B.pt.$_4$mm=154°-156° C. Yield=75.2% b) Preparation of 2,6-dimethyl-4-(3-nitrophenyl)-5-methoxycarbonyl-1,4-dihydropyridine-3-carboxylic acid 2-cyanoethyl ester.

A mixture of 54 g (0.348 mole) of the product obtained in (a), 40 g (0.348 mole) of methyl 3-aminocrotonate and 52.6 g (0.348 mole) of 3-nitro-benzaldehyde, in 500 ml of ethanol is refluxed for 20 hours under an atmosphere of nitrogen.

The hot reaction product is treated with activated charcoal, concentrated to two-thirds, cooled and filtered to produce 101.5 g of a yellow powder.

M.pt.$_{inst.}$ (Kofler)=126° C. Yield=75.8% c) Preparation of 2,6-dimethyl-4-(3-nitrophenyl)-5-methoxycarbonyl-1,4-dihydropyridine-3-carboxylic acid A solution of 19.25 g (0.05 mole) of the product obtained in (b) and 6 g (0.05 mole) of caustic soda pellets in 75 ml of 1,2-dimethoxy-ethane and 150 ml of water is agitated for two hours at room temperature. The reaction product is diluted with water and washed with methylene chloride. The organic phase is then treated with dilute hydrochloric acid and the precipitate removed by filtration.

The product is purified by washing hot with ethanol, giving 14 g of a white powder.

M.pt.=260° C. Yield 84.34% d) Preparation of I-(2,4,6-trimethoxybenzoyl)-3-chloropropane

To a solution of 67.2 g (0.400 mole) of 1,3,5-trimethoxy-benzene and 61 g (0.432 mole) of 4-chloro-butyryl chloride in 300 ml of benzene, maintained at +5° C., a solution of 121 g (0.464 mole) of tin tetrachloride in 160 ml of benzene is added over 3 hrs 30 mins. The mixture is agitated for 4 hours at room temperature and the reaction product is rapidly poured onto 500 ml of iced water and 100 ml of 12N hydrochloric acid. The organic phase is decanted, washed with water and dried with anhydrous sodium sulphate.

The oily residue is washed with hexane, giving 97.2 g of a pale grey powder.

M.pt.$_{inst.}$ (Kofler)=48° C. Yield=89.2% e) Preparation of I-(2,4,6-trimethoxybenzoyl)-3-(3-hydroxypiperidino)propane hydrochloride To a solution of 30 g (0.297 mole) of 3-hydroxy-piperidine in 80 ml of toluene, a solution of 40.5 g (0.148 mole) of the product obtained in example 1(d) in 30 ml of toluene is added over 1 hour under reflux. Reflux is continued for 3 hrs, the reaction product is diluted with ethyl acetate, the insoluble matter is removed by filtration and the filtrate is extracted with a solution of dilute hydrochloric acid. The water phase is made alkaline with caustic soda, which is extracted in turn with ethyl acetate and, after drying with anhydrous sodium sulphate, is treated with hydrochloric isopropanol.

The precipitate obtained by filtration is purified by crystallizing from absolute ethanol, giving 28 g of a white powder.

M.pt.$_{inst.}$ (Kofler)=175° C. Yield=50.7% f) Preparation of 2,6-dimethyl-4-(3-nitro-phenyl)-5-methoxycarbonyl-1,4-dihydropyridine-3-carboxylic acid N-[3-(2,4,6-trimethoxybenzoyl)propyl]piperidine-3'-yl ester, hydrochloride To a solution of 66 ml of dimethylformamide and 38.5 ml of acetonitrile, maintained at −25° C., a solution of 9 g (0.070 mole) of oxalyl chloride in 25 ml of acetonitrile is added over 15 mins. It is agitated for 15 mins at −25° C. and to this is added 16.75 g (0.050 mole) of the product obtained in example 1(c). After 1 hour at −15° C., it is cooled to −25° C. and a solution of 17 g (0.030 mole) of the product obtained in example 1(e) (in the form of base) in 52.5 ml of pyridine and 11 ml of dimethylformamide is added. It is agitated for 20 hours at room temperature and the reaction product is rapidly poured onto 500 ml of iced water and 75 ml of 2N caustic soda and extracted with ethyl acetate. The organic phase is washed with 2N caustic soda, water, 2N hydrochloric acid and a solution of 1N sodium bicarbonate. After drying with anhydrous sodium sulphate, the solvent is evaporated off under reduced pressure, giving a thick orange-coloured oil.

This oil is purified by passing through a silicon gel column and eluted with a mixture of 9 parts of chloroform to 1 part of methanol.

The amorphous product obtained is treated in ethyl acetate with hydrochloric isopropanol. After the precipitate has been triturated in ethyl ether, 24 g of a water-insoluble beige powder is obtained by filtration.

M.pt.=(approximately) 140° C. (forms cohesive mass) Yield=69.8% Total yield=15.2%

EXAMPLE 2

Preparation of 2,6-dimethyl-4-(-3-nitrophenyl)-5-methoxycarbonyl-1,4-dihydropyridine-3-carboxylic acid N-[3-(2,4,6,trimethoxybenzoyl)propyl]piperidine-3-yl ester (CRL 41780)

19.4 g (0.028 mole) of 2,6-dimethyl-4-(3-nitrophenyl)-5-methoxycarbonyl-1,4-dihydropyridine-3-carboxylic acid N-[3-(2,4,6,trimethoxybenzoyl)propyl]piperidine-3-yl ester, hydrochloride (CRL 41695) is treated in water with caustic soda and the precipitate obtained is extracted by ethyl acetate. After drying and evaporation of the solvent, the oily residue is taken up in water and acidified with acetic acid. The solution obtained is treated with activated charcoal and then made alkaline by stirring vigorously with concentrated caustic soda. The precipitate is filtered, giving 15.4 g of a yellow powder which is soluble in water in the presence of acetic acid.

M.pt.=approximately 80° C. (forms cohesive mass) Yield=84.5%

EXAMPLE 3

Preparation of 2,6-dimethyl-4-(3-nitrophenyl-5-methoxycarbonyl-1,4-dihydropyridine-3-carboxylic acid N-[3-(2,4,6-trimethoxybenzoyl)propyl]pyrrolidylmethyl ester, hydrochloride (CRL 41749)

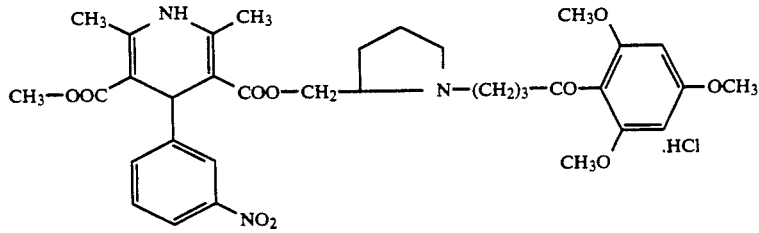

a) Preparation of 1-(2,4,6-trimethoxybenzoyl)-3-chloropropane

To a solution of 67.2 g (0.400 mole) of 1,3,5-trimethoxybenzene and 61 g (0.432 mole) of chloro-4 butyryl chloride in 300 ml of benzene, maintained at +5° C., a solution of 121 g (0.464 mole) of tin tetrachloride in 150 ml of benzene is added over 3 hrs 30 mins. It is agitated for 4 hrs at room temperature and the reaction mixture is rapidly poured onto 500 ml of iced water and 100 ml of 12N hydrochloric acid. The organic phase is decanted, washed with water and dried with anhydrous sodium sulphate. The oily residue is caked by washing with hexane, giving 97.2 g of a light grey powder.

M.pt.$_{inst.}$ (Kofler)=48° C. Yield=89.2% b) Preparation of 1-(2,4,6-trimethoxybenzoyl)-3-(2-hydroxymethylpyrrolidino)propane hydrochloride To a solution of 35.6 g (0.352 mole) of pyrrolidine 2-methanol in 100 ml of toluene, a solution of 48 g of the product obtained in (a) in 40 ml of toluene is added under over 1 hr under reflux. The reflux is maintained for 5 h and the reaction mixture diluted with ethyl acetate. It is then washed with water and extracted with a solution of dilute hydrochloric acid. The water phase is made alkaline with concentrated caustic soda and extracted again with ethyl acetate.

After the organic phase has been dried with anhydrous sodium sulphate, it is treated with hydrochloric isopropanol.

The precipitate obtained is purified by crystallizing from isopropanol, giving 31 g of a water-soluble white powder.

M.pt.$_{inst.}$ (Kofler)=148°-150° C. Yield=47.16 % c) Preparation of 2,6-dimethyl-4-(3-nitrophenyl)-5-methoxycarbonyl-1,4-dihydropyridine-3-carboxylic acid N-[3-(2,4,6-trimethoxybenzoyl)propyl]pyrrolidylmethyl ester.

To a solution of 90 ml of dimethylformamide and 52 ml of acetonitrile, maintained at −25° C., a solution of 12 g of oxalyl chloride in 34 ml of acetonitrile is added over 15 mins. It is stirred for 15 mins at −25° C., then 22.5 g (0.067 mole) of the product obtained in example 1(e) is introduced. After 45 mins at −15° C., the mixture is cooled to −25° C. and a solution of 22.8 g (0.067 mole) of the base product obtained in (b) is poured into 71 ml of pyridine and 15 ml of dimethylformamide. It is stirred for 20 hrs at room temperature, then the reaction mixture is rapidly poured onto 700 ml of iced water and 75 ml of 4N caustic soda and extracted with ethyl acetate. The organic phase is washed with 2N caustic soda, water, 2N hydrochloric acid and a solution of 1N sodium bicarbonate. After drying with anhydrous sodium sulphate, the solvent is evaporated off under reduced pressure, giving an orange-brown coloured oil.

This oil is purified by passing through a silica gel column and eluted with a mixture of 9 parts of methylene chloride to 1 part of methanol.

The amorphous product obtained is treated in ethyl acetate by hydrochloric isopropanol. After triturating the precipitate in ethyl ether, 15 g of a water-insoluble yellow powder is obtained.

M.pt.=(approximately) 120° C. Yield=32.6% Total yield=6.6%

EXAMPLE 4

Preparation of (+)(4S, 3'S) 2,6-dimethyl-4-(3-nitrophenyl)-5-methoxycarbonyl-1,4-dihydropyridine-3-carboxylic acid N-13-(2,4,6-trimethoxybenzoyl)propyl]-piperidine-3'-yl ester (CRL 41859)

a) Preparation of dimethyl 2,6-dimethyl-4-(3-nitrophenyl)-1,4-dihydropyridine-3,5-dicarboxylate A mixture of 75.5 g (0.50 mole) of 3-nitrobenzaldehyde, 116 g (1.00 mole) of methyl acetoacetate and 55 ml (1.50 mole) of 28% ammonia in 150 ml of methanol is heated under reflux for 5 hr.

The precipitate is removed by filtration and the cake purified by hot washing in absolute ethanol, giving 133.5 g of a yellow powder.

M.pt.$_{inst.}$ (Kofler)=208° C. Yield=77.2% b) Preparation of dimethyl 1-ethoxymethyl-2,6-dimethyl-4-(3-nitrophenyl)-1,4-dihydropyridine-3,5-dicarboxylate To a solution of 52 g (0.150 mole) of the product obtained in (a) in 600 ml of tetrahydrofuran, 7.6 g (0.157 mole) of a suspension of 50% sodium hydride in oil is added in portions and stirred for 30 mins at room temperature. A solution of 14.9 g (0.157 mole) of chloromethyl ethyl ether in 50 ml of tetrahydrofuran, at between −20° and −10°C., is then introduced over 15 mins and the mixture stirred for 1 hr 15 mins until it reaches 20° C.

The reaction mixture is taken up in ethyl ether, washed with water, dried with anhydrous sodium sulphate and the solvent evaporated off under reduced pressure. The residue is purified by crystallizing and treated with activated charcoal in diisopropyl ether, giving 47.3 g of a beige powder.

M.pt.$_{inst}$ (Kofler)=86° C. Yield=78.13% c) Preparation of 1-ethoxymethyl-5-methoxycarbonyl-2,6-dimethyl-4-(3-nitrophenyl)-1,4-dihydropyridine-3-carboxylic acid To a solution of 18.7 g (0.813 mole) of sodium in 212 ml of 1-dimethylamino-2-propanol is added a solution of 5.4 ml (0.296 mole) of water in 42 ml of 1-dimethylamino-2-propanol. On cooling in an ice/water bath, a solution of the product obtained in (b) in 270 ml of benzene is introduced over 15 mins. The mixture is stirred at room temperature for 3 hrs and dried under reduced pressure. The residue is cooled in an ice/acetone bath and acidified to pH 2 by the addition of 3N hydrochloric acid. It is then extracted with chloroform, washed with water, dried with anhydrous sodium sulphate and the solvent is evaporated off under reduced pressure.

The residue is purified by passing through a silica column and eluted with a mixture of 4 parts of benzene to 1 part of ethyl acetate, giving 28.5 g of a beige powder.

M.pt.$_{inst.}$ (Kofler)=194° C. Yield=54.9% (Kofler)=194.° C.

d) Preparation of (−) 1-ethoxymethyl-5-methoxycarbonyl-2,6-dimethyl-4-(3-nitrophenyl)-1,4-dihydropyridine-3-carboxylic acid (Kofler)=194° C. 46 g (0.118 mole) of the product obtained in (c) and 34.6 g (0.118 mole) of (−) cinchonidine is dissolved under reflux in 700 ml of methanol and then dried under reduced pressure. The residue is purified by three successive crystallizations from absolute ethanol, giving 19.8 g of a yellow powder.

M.pt.$_{inst.}$ (Kofler)=199° C.

This powder is treated with 0.1N hydrochloric acid and extracted with chloroform. After drying and evaporation of the solvent, 12.7 g of a yellow powder is obtained.

M.pt.$_{inst.}$ (Kofler)=135° C. Yield=27.5% $[\alpha]_D$=−18 (c=1.78, acetone)

e) Preparation of (−)(4R) 5-methoxycarbonyl-2,6-dimethyl-4-(3-nitrophenyl)1,4-dihydropyridine-3-carboxylic acid A solution of 14.8 g (0.0379 mole) of the product obtained in (d) is stirred for one hour at room temperature in 450 ml of acetone in the presence of 90 ml of 1N hydrochloric acid. The reaction mixture is dried under reduced pressure, extracted with ethyl acetate and then washed with water.

After drying and evaporation of the solvent, the residue is purified by washing in ethyl ether, giving 6.4 g of a yellow powder.

Yield=50.9% $[\alpha]_D$=−17 (c=0.5, acetone)

f) Preparation of diacetyl-d-tartaric anhydride

A solution of 40 g (0.266 mole) of D-tartaric acid and 126 ml (1.333 mole) of acetic anhydride is heated slowly under reflux for 10 mins in the presence of 1.2 ml of concentrated sulphuric acid. It is cooled in an ice/water bath for 1 hr and the precipitate filtered and washed with benzene.

The cake is purified by washing with 175 ml of cold ethyl ether, giving 41.7 g of a white powder.

M.pt.$_{inst.}$ (Kofler)=137° C. Yield=72.6% g) Preparation of (−) 4-chlorotartranilic acid

A solution of 40 g (0.185 mole) of the preceding product (f) and 26 g (0.2037 mole) of 4-chloroaniline in 370 ml of methylene chloride is heated under reflux for 3 hr. The reaction mixture is extracted with a solution of 39 g (0.592 mole) of 85% potassium hydroxide in 370 ml of water then by 285 ml of water. The aqueous phases are combined, warmed to 50° C. for 15 mins and acidified with concentrated hydrochloric acid.

The precipitate is filtered and the cake purified by crystallization from a mixture of 50 parts of water and 125 parts of ethanol, giving 48 g of a white powder.

M.pt.=(approximately) 210° C. Yield=(approximately) 100% $[\alpha]_D$=−102 (c=1.6; EtOH 95%)

h) Preparation of (−)(S) 3-hydroxy piperidine 4-chlorotartranilate

A mixture of 46 g (0.177 mole) of the product obtained in (g) and 35.8 g (0.3545 mole) of 3-hydroxy piperidine is heated under reflux, in 350 ml of 95% ethanol, until dissolved. It is crystallized at room temperature, the precipitate filtered and the cake purified by two successive crystallizations from 90% ethanol, giving 52.7 g of white needles.

M.pt.$_{inst.}$ (Kofler)=158° C. Yield=82.6% $[\alpha]_D$=−79 (c=1, H$_2$O)

i) Preparation of (−)(S) 3-hydroxypiperidine

A mixture of 50 g (0.138 mole) of the product obtained in (h) and 19.1 g (0.138 mole) of potassium carbonate, in 336 ml of methanol and 144 ml of toluene, is stirred overnight at room temperature. The insoluble material is removed by filtration and the filtrate dried under reduced pressure.

The residue is caked by washing with ethyl ether, redissolved in a mixture of 7 parts of methanol to 3 parts of toluene, treated with activated charcoal and then dried, giving 13.3 g of a white mass. Yield=95.4% $[\alpha]_D$=−7 (c=2, MeOH)

j) Preparation of (−)(3S) 1-(2,4,6-trimethoxybenzoyl)-3-(3-hydroxypiperidino)propane hydrochloride To a solution of 13 g (0.1287 mole) of the product obtained in (i) in 35 ml of toluene a solution of 17.5 g (0.0643 mole) of 1-(2,4,6-trimethoxybenzoyl)-3-chloropropane obtained in example 1 (d), in 12 ml of toluene, is added under reflux over 1 h. It is refluxed for 2 hrs and the reaction mixture diluted with ethyl acetate. After washing with water, it is extracted with a solution of dilute hydrochloric acid and the aqueous phase made alkaline with concentrated caustic soda and re-extracted with ethyl acetate.

After drying the organic phase with anhydrous sodium sulphate, it is treated with hydrochloric isopropanol.

The precipitate obtained is purified by crystallization from isopropanol, giving 11.4 g of a white powder.

M.pt.$_{inst.}$ (Kofler)=178° C. Yield=47.5%

[α]$_D$=−4.8 (c=2, MeOH)

k) Preparation of (+)(4S, 3'S) 2,6-dimethyl-4-(3-nitrophenyl)-5-methoxycarbonyl-1,4-dihydropyridine-3-carboxylic acid N-[3-(2,4,6-trimethoxybenzoyl)-propyl]piperidine-3'-yl ester (CRL 41859)

To a solution of 15.6 ml of dimethylformamide and 9.1 ml of acetonitrile, maintained at −25° C., a solution of 2.1 g (0.0165 mole) of oxalyl chloride in 6 ml of acetonitrile is added over 15 mins. It is stirred for 15 mins at −25° C., then 3.9 g (0.0118 mole) of the product obtained in (e) is introduced. After 1 hr at −15° C., the mixture is cooled to −25° C. and a solution of 4 g (0.0118 mole) of the base product obtained in (j), in 12.5 ml of pyridine and 2.6 ml of dimethylformamide, is then added. After stirring for 20 hrs at room temperature, the reaction mixture is rapidly poured onto iced water and 25 ml of 2N caustic soda and extracted with ethyl acetate. The organic phase is washed with 2N caustic soda, with water, with 2N hydrochloric acid and with a solution of 1N sodium bicarbonate. After drying with anhydrous sodium sulphate, the solvent is evaporated off under reduced pressure to give a thick orange oil.

This oil is purified by passing through a silica gel column and eluted with a mixture of 95 parts of chloroform to 5 parts of methanol to give, after evaporation of the solvent, 6.2 g of a yellow, water-insoluble, amorphous powder.

M.pt.=(approximately) 80° C. (forms cohesive mass) Yield=80.7%

[α]$_D$=+70 (c 1.25, MeOH)

EXAMPLE 5

Preparation of (−)(4R, 3'R) 2,6-dimethyl-4-(3-nitrophenyl)-5-methoxycarbonyl-1,4-dihydropyridine-3-carboxylic acid N-[3-(2,4,6-trimethoxybenzoyl)propyl]-piperidine-3-yl ester (CRL 41860)

a) Preparation of (+) 1-ethoxymethyl-5-methoxycarbonyl-2,6-dimethyl-4-(3-nitrophenyl)-1,4-dihydropyridine-3-carboxylic acid 46 g (0.118 mole) of the product obtained in example 4(c) and 34.6 g (0.118 mole) of (+) cinchonine are dissolved under reflux in 700 ml of methanol, then dried under reduced pressure. The residue is purified by three successive crystallizations from absolute ethanol, giving 19.8 g of a yellow powder.

M.pt.$_{inst.}$ (Kofler)=215° C.

This powder is treated with 0.1N hydrochloric acid and extracted with chloroform. After drying and evaporation of the solvent 11 g of a yellow powder is obtained.

M.pt.$_{inst.}$ (Kofler)=134° C. Yield=24%

[α]$_D$=+15 (c=1.90, acetone)

b) Preparation of (+)(4S) 5-methoxycarbonyl-2,6-dimethyl-4-(3-nitrophenyl)-1,4-dihydropyridine-3-carboxylic acid A solution of 13.8 g (0.035 mole) of the product obtained in (a) is stirred for 1 hr in 420 ml of acetone in the presence of 85 ml of 1N hydrochloric acid. The reaction mixture is dried under reduced pressure, extracted with ethyl acetate then washed with water.

After drying and evaporation of the solvent, the residue is purified by washing with ethyl ether to give 6.4 g of a yellow powder.

Yield=55% [α]$_D$=+18 (c=0.5, acetone)

c) Preparation of (+) diacetyl-d-tartaric anhydride.

A solution of 40 g (0.266 mole) of L-tartaric acid and 126 ml (1.333 mole) of acetic anhydride is slowly heated under reflux for 10 mins in the presence of 1.2 ml of concentrated sulphuric acid. The mixture is cooled in a water/ice bath for 1 hr and the precipitate filtered and washed with benzene.

The cake is purified by washing with 175 ml of cold ethyl ether, giving 42.5 g of a white powder.

M.pt.$_{inst.}$ (Kofler)=136° C. Yield=74% d) Preparation of (+) 4-chlorotartranilic acid

A solution of 40 g (0.1850 mole) of the product obtained in (c) and 26 g (0.2037 mole) of 4-chloroaniline in 370 ml of methylene chloride is heated under reflux for 3 hrs. The reaction mixture is extracted with a solution of 39 g (0.592 mole) of 85% potassium hydroxide in 370 ml of water then by 185 ml of water. The aqueous phases are combined, warmed to 50° C. for 15 mins and acidified with concentrated hydrochloric acid.

The precipitate is filtered and the cake purified by crystallization from a mixture of 50 parts of water to 125 parts of ethanol, giving 46.6 g of a white powder.

M.pt.=(approximately) 210° C. Yield=97%

[α]$_D$=+103 (c=1.6; EtOH 95%)

e) Preparation of (+)(R) 3-hydroxy piperidine 4-chlorotartranilate

A mixture of 45 g (0.173 mole) of the product obtained in (d) and 35 g (0.357 mole) of 3-hydroxy piperidine, in 350 ml of 95% ethanol, is heated under reflux until dissolved. The mixture is allowed to crystallize at room temperature, the precipitate filtered and the cake purified by two successive crystallizations from 85% ethanol, giving 51.6 g of white needles.

M.pt.$_{inst.}$ (Kofler)=158° C. Yield=82.7% [α]$_D$=+80 (c=1, H$_2$O)

f) Preparation of (+)(R) 3-hydroxypiperidine

A mixture of 50 9 (0.138 mole) of the product obtained in (e) and 19.1 g (0.138 mole) of potassium carbonate, in 336 ml of methanol and 144 ml of toluene, is stirred overnight at room temperature.

The insoluble material is removed by filtration and the filtrate dried under reduced pressure.

The residue is caked by washing with ethyl ether, redissolved in a mixture of 7 parts of methanol to 3 parts of toluene, treated with activated charcoal then dried to give 13.3 g of a white mass.

Yield=95.4% [α]$_D$=+8 (c=2, MeOH)

g) Preparation of (+)(3R) 1-(2,4,6-trimethoxybenzoyl)-3-(3-hydroxypiperidino)propane hydrochloride.

To a solution of 12.7 g (0.1257 mole) of the product obtained in (f) in 35 ml of toluene, a solution of 17.1 g (0.0628 mole) of the product 1-(2,4,6-trimethoxybenzoyl)-3-chloropropane obtained in example 1(d), in 12 ml of toluene, is added over 1 hr under reflux. The reaction mixture is refluxed for 2 hrs and then diluted with ethyl acetate. After washing with water, it is extracted with a solution of dilute hydrochloric acid, then the aqueous phase made alkaline with concentrated caustic soda and a re-extracted with ethyl acetate.

After drying the organic phase with anhydrous sodium sulphate, it is treated with hydrochloric isopropanol.

The precipitate obtained is purified by crystallization from isopropanol, giving 10.1 g of a white powder.

M.pt.$_{inst.}$ (Kofler)=178° C. Yield=47.06%

[α]$_D$=+5.4 (c=2, MeOH)

h) Preparation of (−)(4R, 3'R) 2,6-dimethyl-4-(3-nitrophenyl)-5-methoxycarbonyl-1,4-dihydropyridine- 3-carboxylic acid N-[3-(2,4,6-trimethoxybenzoyl)-propyl]piperidine-3'-yl ester (CRL 41860)

To a solution of 16.4 ml of dimethylformamide and 9.6 ml of acetonitrile, maintained at −25° C., a solution of 2.2 g (0.0173 mole) of oxalyl chloride in 6.2 ml of acetonitrile is added over 15 mins. The mixture is stirred for 15 mins at −25° C., then 4.1 g (0.0124 mole) of the product obtained in (b) is introduced. After 1 hr at −15° C., the mixture is cooled to −25° C. and a solution of 4.2 g (0.0124 mole) of the base product obtained in (g) in 13 ml of pyridine and 2.71 ml of dimethylformamide is added. After stirring for 20 hrs at room temperature, the reaction mixture is rapidly poured onto 125 ml of iced water and 20 ml of 2N caustic soda then extracted with ethyl acetate. The organic phase is washed with 2N caustic soda, with water, with 2N hydrochloric acid and with a solution of 1N sodium bicarbonate. After drying with anhydrous sodium sulphate, the solvent is evaporated under reduced pressure to give a thick orange oil.

The oil is purified by passing through a silica gel column and eluted with a mixture of 95 parts of chloroform to 5 parts of methanol to give, after evaporation of the solvent, 4.35 g of a yellow, water-insoluble, amorphous powder.

M.pt=(approximately) 80° C. (forms cohesive mass)
Yield=53.9%
$[\alpha]_D = -60$ (c=1.25, MeOH)

EXAMPLE 6

Preparation of (+)(4R, 3'S) 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine-3'-yl ester (CRL 41862)

To a solution of 18.7 ml of dimethylformamide and 11 ml of acetonitrile, maintained at −25° C., is added a solution of 2.5 g (0.0198 mole) of oxalyl chloride in 7.2 ml of acetonitrile. The mixture is stirred for 15 min at −25° C., then 4.7 g (0.0142 mole) of the product obtained in 5(b) is introduced. After 1 hr at −15° C., the mixture is cooled to −25° C. and a solution of 4.8 g (0.0142 mole) of the base product obtained in example 4(j) in 15 ml of pyridine and 3.1 ml of dimethylformamide is added. After stirring for 20 hr at room temperature, the reaction mixture is rapidly poured onto 130 ml of iced water and 25 ml of 2N caustic soda then extracted with ethyl acetate. The organic phase is washed with 2N caustic soda, with water, with 2N hydrochloric acid and with a solution of 1N sodium bicarbonate. After drying with anhydrous sodium sulphate, the solvent is evaporated under reduced pressure to give a thick orange oil.

This oil is purified by passing through a silica gel column and eluted with a mixture of 95 parts of chloroform to 5 parts of methanol to give, after evaporation of the solvent, 5.9 g of a yellow, water-insoluble, amorphous powder.

M.pt.=(approximately) 80° C. (forms cohesive mass)
Yield=63.8% $[\alpha]_D = +6$ (c=1.25, MeOH)

EXAMPLE 7

Preparation of (−)(4S, 3'R) 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine-3'-yl ester (CRL 41863)

To a solution of 15.6 ml of dimethylformamide and 9.1 ml of acetonitrile, maintained at −25° C., a solution of 2.1 9 (0.0165 mole) of oxalyl chloride in 6 ml of acetonitrile is added over 15 mins. The mixture is stirred for 15 mins at −25° C., then 3.9 g (0.0118 mole) of the product obtained in 4(e) is introduced. After 1 hr at -15° C., the mixture is cooled to −25° C. and a solution of 4 g (0.0118 mole) of the base product obtained in example 5(g) in 12.5 ml of pyridine and 2.6 ml of dimethylformamide is added. After stirring for 20 hrs at room temperature, the reaction mixture is rapidly poured onto 120 ml of iced water and 25 ml of 2N caustic soda then extracted with ethyl acetate. The organic phase is washed with 2N caustic soda, with water, with 2N hydrochloric acid and with a solution of 1N sodium bicarbonate. After drying with anhydrous sodium sulphate, the solvent is evaporated off under reduced pressure to give a thick orange oil.

The oil is purified by passing through a silica gel column and eluted with a mixture of 95 parts of chloroform to 5 parts of methanol to give, after evaporation of the solvent, 3 g of a yellow, water-insoluble, amorphous powder.

M.pt.=(approximately) 80° C. (forms cohesive mass)
Yield=39% $[\alpha]_D = -11$ (c=1.25, MeOH)

EXAMPLE 8

Preparation of (+)(4S, 3'S)/(−)(4R, 3'R) 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine-3'-yl ester, hydrochloride (CRL 41886)

A solution of 20 g (0.030 mole) of the compound obtained in example 2 in 100 ml of acetone is treated with 8 ml of hydrochloric isopropanol. It is stirred and left at room temperature for 4 days.

The crystallized product is filtered and then washed with hot isopropanol to give 8.3 g of a water-insoluble yellow powder.

M.pt.=205° C. Yield=39.3%

EXAMPLE 9

Preparation of (+)(4S, 3'R)/(−)(4R, 3'S) 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine-3'-yl ester, hydrochloride (CRL 41887)

A solution of 20 g (0.030 mole) of the compound obtained in example 2 in 100 ml of acetone is treated with 8 ml of hydrochloric isopropanol. It is stirred and left at room temperature for 4 days.

The crystallized product is removed by filtration. The filtrate, after treatment with activated charcoal, is dried under reduced pressure and the sticky residue is caked by washing twice with ethyl acetate.

The crystallized product obtained is purified by washing with hot isopropanol to give 3.5 g of a water-insoluble, yellow powder.

M.pt.=212° C. Yield=24.6%

EXAMPLE 10

Preparation of 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine-3'-yl, lactate (CRL 41813)

150 ml of distilled water, 10 g (0.0153 mole) of the compound obtained in example 2 and 1.4 g (0.0153 mole) of tactic acid are mixed.

After stirring overnight at room temperature, the solution is treated with activated charcoal and dried under reduced pressure. 9 g of an amorphous yellow powder is obtained, which is soluble in cold water but is precipitated on warming.

Forms cohesive mass Yield = 86.75%

EXAMPLE 11

Preparation of 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine-3'-yl ester, glutamate (CRL 41814)

9 g (0.0138 mole) of the compound obtained in example 1 and 2.3 g (0.0138 mole) of hydrated glutamic acid in 50 ml of methanol are mixed. After stirring at room temperature, the solution is dried under reduced pressure.

11 g of an water-insoluble, amorphous yellow powder is isolated.

Forms cohesive mass Yield = 99%

EXAMPLE 12

Preparation of 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine-3'-yl ester, aspartate (CRL 41815)

10 g (0.0153 mole) of the compound obtained in example 2 and 2.05 g (0.0153 mole) of aspartic acid in 100 ml of methanol and 150 ml of distilled water are mixed. After stirring at room temperature, the solution obtained is evaporated under reduced pressure to give 10.5 g of an water-insoluble, amorphous yellow powder.

Forms cohesive mass Yield = 87.5%

The toxicological and pharmacological results set out below demonstrate clearly the properties of the compounds according to the invention.

1) Acute toxicity

The acute toxicity of the compound of example 1 was determined on rats injected intraperitoneally (Sprague-Dawley rats) and the product was administered as a 20 mg/ml aqueous suspension.

$LD_{50} = 249 \pm 50$ mg/kg

As a comparison, the $LD_{50}$ of nicardipine determined under the same conditions was $233 \pm 65$ mg/kg.

2) Calcium blocking activity

The calcium blocking activity was determined in vitro by using the method of contracting the rat's isolated aorta with KCI (see Bernard Swynghedauw—Animal Experiments in Cardiology, Collection INSERM Medicine Sciences, Flammarion).

For this purpose, the $IC_{50}$ values were at first determined at the receptors (on the DHP membranous site with $^3$H-radiolabelled ligand isradipine and with these doses the percentage of inhibition in the contraction of the isolated aorta was determined.

The results were as follows:

| Compound tested Example | Dose (M) | % inhibition |
| --- | --- | --- |
| 2 | $10^{-8}$ | 60 |
| 4 | $3 \times 10^{-9}$ | 70 |
| 7 | $2 \times 10^{-9}$ | 80 |
| 8 | $4 \times 10^{-9}$ | 40 |
| 9 | $6 \times 10^{-10}$ | 60 |

3) Effects on mean arterial pressure and heartbeat frequency

The effects were tested using conscious Wistar rats suffering from genetic hypertension (6 rats per compound). The compounds were administered orally as a 16 mg/kg (under 5.3 ml/kg) dose in suspension.

The results were as follows:

|  | CRL 41695 | Nicardipine |
| --- | --- | --- |
| Arterial pressure |  |  |
| Variation after 3 hrs | −50% | −39% |
| Variation after 7 hrs | −42% | −27% |
| Heartbeat frequency |  |  |
| Variation after 5 mins | +13% | +32% |
| Variation after 5 hrs | 0% | +23% |

With the Example 1 compound, hypo tension was found to be significantly raised during at least 7 hours. Heartbeat frequency was only slightly increased by the Example 1 compound, whereas nicardipine produced a clear tachycardic effect after five minutes.

A secondary tachycardiae effect was also observed with nicardipine, attaining its maximum effect after 5 hours. Such a tachyeardiac effect was not found with the Example 1 compound.

4) Effect on histamine hyperpermeability

The effect of CRL 41695 administered intraperitoneally on hystamine hyperpermeability was tested on Sprague-Dawley rats.

The parameter tested was the effect on Evan's Blue intradermal extravasation induced by histamine injection.

24 hours after shaving and epilation of the rat's flanks, CRL 41695 was injected intraperitoneally at dose levels of 10 mg/kg (dispersed in 0.9% NaCl +5% carboxymethylcellulose) and 10 minutes later 0.25 ml/100 g of Evan's Blue at 2% injected intravenously.

0.1 ml of 0.9% NaCl was then injected intradermally in the left flank and 0.01 ml of histamine (50 pg) in the right flank.

The rats were sacrificed after 40 minutes and the injection sites removed. The Evan's Blue was extracted from the skin with 65% formamide and the solvent was removed by filtration. The optical density was determined as 620 nm.

In comparison with the reference solution (NaCl solution) a 50% decrease in the intradermal concentration of Evan's Blue was observed.

At a dose level of 10 mg/kg administered intraperitoneally, the Example 1 compound was therefore found to decrease greatly the intradermal concentration of Evan's Blue induced by histamine and was therefore shown to have an antihyperpermeable effect.

The present invention also has for its object therapeutic compositions containing as an active principle a compound according to formula I or one of its addition salts with pharmaceutically acceptable acids.

The therapeutic compositions according to the invention administered to humans or animals orally or parenterally.

They may be in the form of solid, semisolid or liquid preparations, for example compressed tablets, capsules, suppositories, injectable solutions or suspensions, as well as delayed-release preparations and slow-release implants.

In these compositions, the active principle is normally mixed with one or several commonly used pharmaceutically acceptable excipients which are well known by those skilled in the art.

The quantity of active principle administered obviously depends on the patient being treated, on the method of administration and the severity of the illness.

Owing in particular to their effect on hyperpermeability, the compositions according to the invention are particularly suitable for the treatment of peripheral oedemas and in renal tissue protection of patients with kidney insufficiency and diabetics.

I claim:

1. A compound selected from the compounds having the formula:

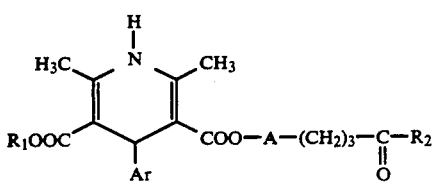

in which:

Ar represents a group selected from 2-nitrophenyl, 3-nitrophenyl, 2-chlorophenyl, 2,6-dichlorophenyl, 2-trifluoromethylphenyl and 3-trifluoromethylphenyl;

$R_1$ represents a $C_1$–$C_4$ alkyl group or a group having the formula:

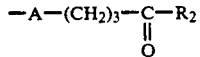

A represents a group selected from the groups with the formulae:

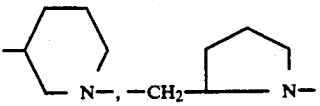

and $R_2$ represents a group selected from 2,4,6-trimethoxyphenyl, and their addition salts with pharmaceutically acceptable acids.

2. A compound according to claim 1, selected from 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine- 3'-yl ester, and its addition salts with pharmaceutically acceptable acids.

3. A compound according to claim 2, selected from (+) (4S, 3'S) 2,6-dimethyl-4-(3-nitrophenyl)-5-methoxycarbonyl-1,4-dihydropyridine-3-carboxylic acid N-[3-(2,4,6-trimethoxybenzoyl)propyl]piperidine-3'-yl ester, and its addition salts with pharmaceutically acceptable acids.

4. A compound according to claim 2, selected from (−) (4S, 3'R) 2,6-dimethyl-4-(3-nitrophenyl)-5-methoxy-carbonyl-1,4-dihydropyridine-3-carboxylic acid N-[3-(2,4,6-trimethoxybenzoyl)propyl]piperidine-3'-yl ester, and its addition salts with pharmaceutically acceptable acids.

5. A therapeutic composition having an antihypertensive activity comprising an effective amount of a compound according to claim 1 and a therapeutically acceptable excipient.

6. A therapeutic composition having an antipermeable effect comprising an effective amount of a compound according to claim 1 and a therapeutically acceptable excipient.

7. A process for the treatment of hypertension which comprises administering to a human in need thereof an effective amount of a compound according to claim 1.

* * * * *